US008628980B2

(12) United States Patent
Willson et al.

(10) Patent No.: US 8,628,980 B2
(45) Date of Patent: Jan. 14, 2014

(54) OPTICAL MICROLABELS: SHAPES AND REFLECTORS

(76) Inventors: Richard C. Willson, Houston, TX (US); Raul Ruchhoedft, Calgary (CA)

( * ) Notice: Subject to any disclaimer, the term of this patent is extended or adjusted under 35 U.S.C. 154(b) by 0 days.

(21) Appl. No.: 13/562,260

(22) Filed: Jul. 30, 2012

(65) Prior Publication Data

US 2013/0034498 A1 Feb. 7, 2013

Related U.S. Application Data

(62) Division of application No. 12/769,169, filed on Apr. 28, 2010, now Pat. No. 8,232,112, which is a division of application No. 11/257,566, filed on Oct. 25, 2005, now Pat. No. 7,727,775.

(60) Provisional application No. 60/621,706, filed on Oct. 25, 2004.

(51) Int. Cl.
*G01N 33/543* (2006.01)

(52) U.S. Cl.
USPC ..................... 436/518; 422/82.05; 435/287.2; 435/288.7; 436/164; 436/172; 436/805; 977/701; 977/702; 977/704; 977/705; 977/773; 977/774; 977/834; 977/920

(58) Field of Classification Search
None
See application file for complete search history.

(56) References Cited

U.S. PATENT DOCUMENTS

| | | | | |
|---|---|---|---|---|
| 7,727,775 B2 * | 6/2010 | Willson et al. | ................ | 436/518 |
| 8,232,112 B2 * | 7/2012 | Willson et al. | ................ | 436/518 |

* cited by examiner

*Primary Examiner* — Chris L Chin
(74) *Attorney, Agent, or Firm* — Robert W Strozier

(57) ABSTRACT

Labels and methods of producing labels for use in clinical, analytical and pharmaceutical development assays are provided. Labels may comprise shape-encoded particles which may be coupled to ligands such as DNA, RNA and antibodies, where different shapes are used to identify which ligand(s) are present. Labels may also comprise reflectors, including retroreflectors and retroreflectors susceptible to analyte-dependent assembly for efficient homogeneous assays.

5 Claims, 7 Drawing Sheets

OPTICAL MICROLABELS: SHAPES AND REFLECTORS

RELATED APPLICATIONS

This application is a divisional application of Ser. No. 12/769,169, filed on 28 Apr. 2010, now U.S. Pat. No. 8,232,112, which is a divisional application of Ser. No. 11/257,566, filed on 25 Oct. 2005, now U.S. Pat. No. 7,727,775, which claims provisional priority to U.S. Provisional Application Ser. No. 60/621,706, filed on 25 Oct. 2004.

BACKGROUND OF THE INVENTION

1. Field of the Invention

The present invention relates to the use of micron-scale labels for use primarily in monitoring DNA hybridization, antibody-based immunoassays, and cellular functioning.

More particularly, the present invention relates to micron-scale shapes and reflectors, particularly retroreflectors, with highly detectable and information-rich optical properties. This invention also relates to a class of micron-scale labels made of inorganic materials, capable of high information content, and not subject to photobleaching. One class of such labels offers extremely high detectability. Primary uses for these labels are envisioned to be in DNA probe, DNA array assays, and immunoassays.

2. Description of the Related Art

Retroreflectors are widely used in road and safety signs, as misalignment-tolerant optical components, and in retroreflective paints, e.g., for lane markers. Retroreflectors are commonly used in the form of sheets of retroreflective film bearing cubical or spherical retroreflectors, arrays of large (centimeter-scale) reflectors for object detection and ranging, and spherical elements with reflective backing for safety and road markings. The background art does not provide for the use of micron-scale retroreflectors, singly or in arrays, with or without self-assembly, associated with biological recognition elements, in bioassays and biosensors.

The essential components of a bioassay are a molecular recognition element, and a label used to determine whether the recognition element is bound to a target.

Labels in current use include fluors, colored particles, and enzymes used with chromogenic, fluorogenic or chemiluminescent substrates. These suffer from a variety of drawbacks, including photobleaching, high cost, poor storage stability, competing activities in biological samples (enzymes and indigenous fluors), mutual quenching, limited detectability, and limited multiplex-ability.

Thus, there is a need in the art for stable, highly-detectable labels for bioassays and biosensors having enhanced information content and capable of self-assembling to provide low-labor assays and biosensors.

SUMMARY OF THE INVENTION

The present invention provides for the use of modern parallel micro- and nano-fabrication methods to produce superior taggants and labels of several types. One type will be unique shape-encoded labels which can be optically differentiated (like written labels or bar codes). These would be useful in assays where many different species are to be identified/quantitated in the same sample. Another type will be reflectors and retroreflectors, miniature versions of perhaps the most detectable objects ever made by humans. These offer the advantage of superior detectability, allowing remote analysis and the use of relatively simple readers, and are amenable to self-assembly as the basis of simple, and in vivo assays and biosensors.

The present invention also provides a self-assembly basis for simple, no-wash immunoassays, where the presence of a target analyte produces a change in retroreflection intensity.

The present invention provides labels and biosensors which can be used in the body for detection of glucose, lactate, and cancerous or diseased tissues.

The present invention also provides a method for facilitating exploiting the olfactory and flight powers of birds, bats or insects for searching and identifying objects of interest, especially illicit drugs and explosives such as land mines.

The present invention provides a means for production of security identification devices and taggants for explosives, pharmaceuticals, etc. which are extraordinarily difficult to counterfeit.

BRIEF DESCRIPTION OF THE DRAWINGS

The invention can be better understood with reference to the following detailed description together with the appended illustrative drawings in which like elements are numbered the same:

FIG. 13 shows a linear retroreflector illuminated in a non-retroreflecting configuration, where the dark regions in the image are structures that were etched into a 5 micron thick layer of polyimide; and.

DETAILED DESCRIPTION OF THE INVENTION

Figure 1A:
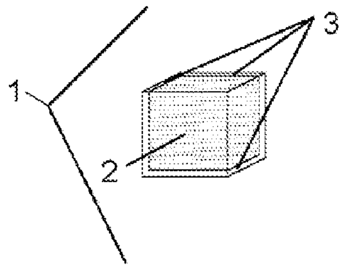
FIG. 1*a* depicts a corner cube retroreflector.

The inventors have found that retroreflectors can be manufactured having generally regular solid geometrical shapes such as cubes that having reflective and non-reflective sides capable of chemical modification and that the tags with or without modification can be used as a detection platform, an identification platform or in any application where the ability visibly identify, track or code a item would be needed or desired.

Also, there is an ongoing desire within the law enforcement communities to have a way of recognizing or tracing explosives and other materials that have been used in a crime. It will be appreciated that a useful taggant will need to satisfy a number of challenging performance requirements. First, the taggant material must be easily and cheaply dispersed throughout a batch of explosive material using traditional formulating and blending equipment. At the same time, explosives, by their very nature, must be formulated carefully and the industry is understandably reluctant to add materials that might make them unstable or unpredictable. In particular, taggants made from small bits of plastic might be a source of static electricity that could lead to catastrophic detonation during processing, mixing, or loading cartridges. Users will also balk if the performance of the explosive is degraded or if significant costs are added. For the taggant particles to be useful, they must be easily recovered at a crime scene. This means they must first survive and then be detectable (found and collected) at the scene with simple equipment. They must also retain enough of their original distinctive properties to meet the standards of legal evidence. Among other things, this means that the taggant particles must be easily distinguished from other natural or man-made particles such as minerals, cement, fly ash, smelting residues, and the like. The reflectors and shapes of the present invention can meet these requirements.

While several tagging methodologies and methods for tagging sensitive materials such as explosives have previously been developed, the tags, the methods for making the tags and the methods for using the tags of this invention are ideally suited for tagging such articles as explosives, munitions, ammunition, or other articles used by law enforcement or the military.

Other technologies currently available utilize colored or magnetic particles that can be recovered in the field and then "read" by recognizing some distinguishing characteristic such as the pattern of colored bands or a distinctive spectral response. Powdered phosphor materials potentially satisfy several of the aforementioned requirements for use as taggants. They are bright (i.e. only a small amount is needed in order to be detected), each material exhibits its own unique optical characteristics that can be easily detected, and they are compatible with common bullet and propellant materials. Some of the best candidate materials are ceramics, and are thus capable of enduring harsh environments with no impact on their optical functionality.

A fluorescent tagging means for pre-detonation or post-detonation identification of explosives is described. A combination of "spotting" phosphor, which is excitable by ultraviolet radiation to provide a band-type emission and "coding" phosphors, which emit a line-type emission, were added to explosives. All of the phosphors have very small particle sizes and are incorporated into phosphor grains held together by inorganic cement or a binder, and the resulting conglomerate grains are dispersed in the explosive. After an explosion, the phosphor grains can be readily located by the ultraviolet response of the spotting phosphor, and information disclosed by the presence (or absence) of the coding phosphor can then be decoded. The spotting phosphor will also normally provide some additional indicia of information.

To inhibit any tendency for the phosphor conglomerate particles to sensitize the explosives, the individual particles can be encapsulated in an organic plastic material such as polyethylene. These encapsulated particles can incorporate an anti-static coating, such as amorphous carbon, in order to prevent electrostatic charging thereof.

Also microparticles for tagging of explosives, which particles incorporate a substantial proportion of magnetite that enables the particles to be located by means of magnetic pickup. Ferrite has also been used. More recently, modified tagging particles with strips of color coding material having a layer of magnetite affixed to one side and layers of fluorescent material affixed to both exterior sides, has been developed. In this system, the taggant can be located by visual detection of the luminescent response, or magnetic pickup, or both. Both the ferrite and the magnetite materials are, however, dark colored and absorptive of the radiation which excites the luminescent material, thereby making the particles somewhat difficult to locate after an explosion. Further developments produced similar particles that take advantage of the magnetic properties without diminishing the luminescent response of the materials.

Yet another approach is the development of particles coded with ordered sequences of distinguishable colored segments. Other patents employ radioactive isotopes or other hazardous materials as taggants. Such taggants and labels can also be employed to prove authenticity, e.g. in perfumes, lubricants, pharmaceuticals and other valuable materials that are likely to be counterfeited.

Competing tags and tagging methodologies can be found in U.S. Pat. Nos. 3,772,099; 3,897,284; 3,967,990; 3,993,838; 4,053,433; 4,131,064; 6,899,827, incorporated herein by reference.

1. Shape-Encoded Labels

Current Approach:

The fabrication of microarrays involves the placement of unique probes in a fixed array on a support substrate. Although the microarray fabrication process is well developed, well understood, and commonly used, it is not well suited for low-cost manufacturing because of the serial nature of the array formation. Typically, a single nozzle dispenses probes in solution at fixed points, limiting both the spatial density and the fabrication throughput.

In the present invention, we instead place probes on micron-sized shape labels whose shape is unique and can easily be identified using standard microscopic analysis (either by optical or scanning electron microscopy). We can use a low-cost lithographic process to fabricate a large number of the shapes on a single carrier wafer and attach a particular probe (DNA or analog, peptide, protein, etc.) to all tiles in a single step. Once the probes have been attached, the tiles are released from the substrate, disperse/suspended into solution, and can be mixed with shapes from wafers containing different probes. The solution can then be mixed with the specimen to be examined and then dried on a carrier substrate. By using a unique shape for each probe, we can effectively create an array microarray without any spatial order and, when attachment to a probe has been detected, the probe type can be readily identified by examining the underlying shape.

While microarrays rely on the known position of the probes for detection, shape detection relies on subsequent identification of the tile shape. Nicewarner-Pena et al. have described a similar approach, where the probes are attached to long, barcoded rods. Our use of shaped tiles is believed to be more flexible, providing significantly more information to be stored in a smaller amount of space. Our fabrication is expected to be more efficient, as well.

While we present here one method for fabricating these tiles, a large number of alternative methods can easily be used to achieve the same end result. The choice of implementation is ultimately dictated by the cost of the fabrication steps. However, a preferred common theme in all fabrication approaches is the high-throughput lithographic technique used to define the unique shapes.

Figure 7:
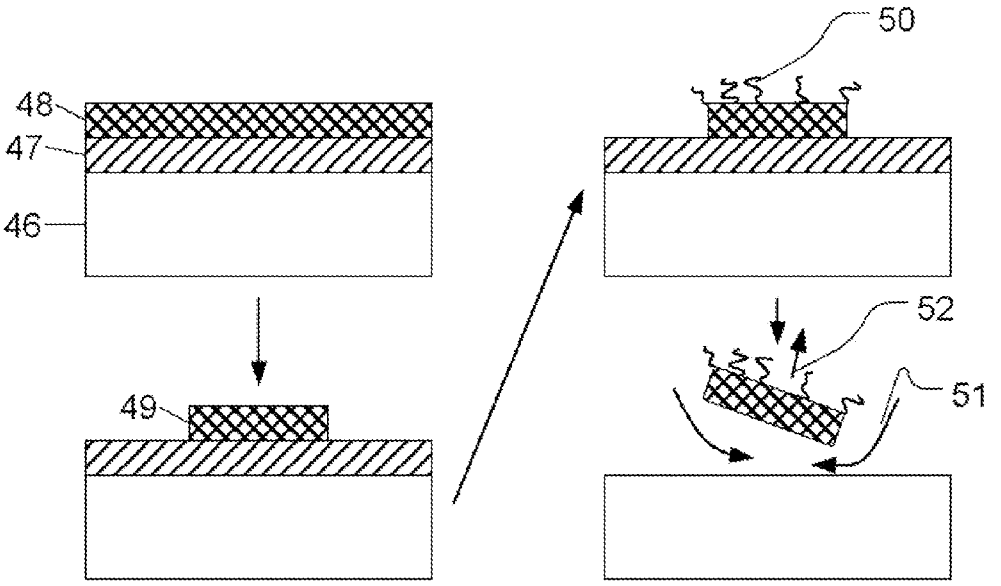
FIG. 7 depicts another embodiment of a fabrication process of making another form of reflectors of this invention.

An embodiment of a process of this invention includes the steps as depicted in FIG. 7. (1) A substrate is coated with a release layer and HSQ photoresist. The release layer should be soluble in a solution that does not damage the probes. (2) The resist is patterned using ion beam proximity lithography (IBP), atom beam lithography (ABL), or any other lithographic technique with adequate resolution and throughput. During development, the unexposed regions wash away, leaving behind silica island structures. Any number of alternative multi-layer lithography steps can be used in place of the negative tone HSQ resist, including tone reversal steps and bi-layer resist processing. (3) The probes are attached to the substrate surface and (4) the release layer is dissolved so that the islands are freed from the substrate surface.

An example of a shape that could be employed consists of a base shape which is a primary rectangle and a smaller, secondary rectangle that adjoins the first at one of the corners. This asymmetric shape is chosen to ensure that its orientation can be determined, including whether or not the island is upside-down. A set of squares is used to label the shape, yielding a total of 2' possible combinations, where n is the number of squares. In this example, eight squares allows for the creation of 256 unique shapes, used to identify 256 different labels. The size of the shapes can also be used to increase the number of unique possibilities.

Finally, another variation of this process would rely on self-assembly of the shapes into pre-defined locations on the substrate. The advantage in this hybrid approach is that the island structures are fabricated in parallel on the carrier wafer but, by assembling the shapes into a known configuration, the shape detection step can be avoided.

2. Reflectors

These are tiny mirrors and retroreflectors. In most applications, they would have attached to them a biological targeting ligand, as discussed in Table B below.

Flat mirrors are highly detectable, but only from a limited viewing angle (shine a flashlight into a mirror in a dark room; the image is blindingly bright (only) when the beam returns to the viewer's eye. This viewing angle is typically determined by the numerical aperture of the imaging optics and can be significantly large. Table A shows the maximum tilt in a planar mirror that would still be detectable using standard optical microscope objectives. Most noteworthy is that a planar mirror can lie at an angle of >41° and the reflected light will still enter a 40× microscope objective. Putting them on a cell (e.g., by antibody to surface antigens) or inside a cell (by uptake signals) might usefully signal cell metabolic activity and/or motility, e.g., in drug screening or toxin detection.

TABLE A

Maximum Detectable Mirror Angle for Various Standard Optical Objectives

| Magnification | NA | Resolution lp/mm | Resolution μm | DOF (μm) | WD* (mm) | FOV** (mm × mm) | CCD Resolution** (μm) | Max. mirror angle (deg) |
|---|---|---|---|---|---|---|---|---|
| 4x | 0.1 | 300 | 1.7 | 54.7 | 21.8 | 1.5 × 1.2 | 2.7 | 6 |
| 10x | 0.25 | 750 | 0.7 | 8.5 | 6.14 | 0.6 × 0.5 | 1.1 | 14 |
| 20x | 0.4 | 1200 | 0.4 | 3.2 | 3.3 | 0.3 × 0.25 | 0.5 | 24 |
| 40x | 0.65 | 1950 | 0.3 | 1.0 | 0.48 | 0.15 × 0.12 | 0.2 | 41 |

*Objectives are 20.5 mm wide
**0.6 × 0.5 mm CCD with 550 lines

Diamond-cut reflectors return light in multiple narrow beams, enhancing detectability by correctly-positioned detectors.

Retroreflectors (references 1-9) act as mirrors, which, over a broad angle, return light toward its source, as shown schematically in FIG. 1. These have extremely high detectability using simple illumination and detection (e.g., epi-illumination in a microscope with a semi-silvered mirror but no wavelength filters). In fact, a set of corner-cube retroreflectors on the lunar surface is routinely detected and ranged as part of ongoing experiments on lunar orbital dynamics (for additional information see, e.g., www.jpl.nasa.gov/news/features.cfm?feature=605). Retroreflectors can be based on hemispherical or corner-cube elements; fabrication of corner-cube retroreflectors is illustrated in FIG. 2.

Figure 10:
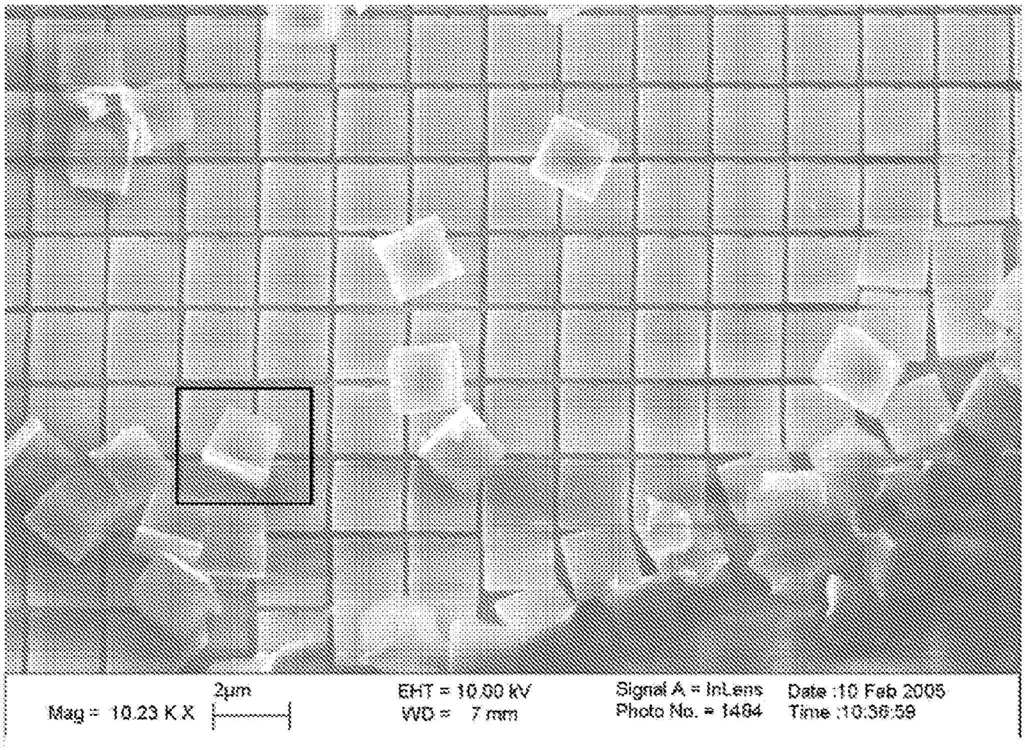
FIG. 10 shows an array of micro-fabricated polyimide cube structures where some of the cubes have been mechanically removed from the surface for the purpose of viewing.

Described here is the procedure for fabricating the structures shown in FIG. 10. A glass substrate was coated with a nominally 1.5 micrometer thick layer of polyimide by spin-casting a solution of Durimide 285 solution (Arch Chemical, Norwalk, Conn.) for approximately 2 min, followed by a 2 minute bake at 90 degrees Centigrade and a 2 hour bake at 180 degrees Centigrade on a planar hot-plate. The polyimide was then coated with approximately 80 nm of nonstoichiometric silicon dioxide in a sputter-deposition chamber containing a 5 cm planar magnetron sputtering gun (Angstrom Sciences, Duquesne, Pa.) and a mixture of argon and 10% oxygen at a pressure of 2.13 Pa (16 mTorr). An approximately 200 nm thick layer of poly(methyl methacrylate) (PMMA) was then deposited by spin-casting a solution of 950 Kg/mol a solution of 4.5% PMMA dissolved in chlorobenzene for 30 seconds and the sample was baked at 180 degrees Centigrade for 1 hour.

The sample was loaded into a custom ion-beam lithography tool, and a pattern of approximately 9 million intersecting, mutually touching, orthogonal lines, with 2 micrometer pitch, was printed using an ion beam aperture array lithography process. The exposed regions of the PMMA were washed away after removing the sample from the lithography tool by dip-development in a solution of equal parts of methyl isobutyl ketone and isopropanol. An example of the resulting PMMA pattern can be seen in FIG. 12. The PMMA pattern was then transferred into the underlying silicon dioxide layer by $CHF_3$ reactive ion etching in an in-house magnetically enhanced reactive ion etcher. The system pressure was approximately 0.7 mTorr, and 85 watts of radio frequency (RF) power was applied to ignite the plasma and etch the sample. The silicon dioxide acted as a mask for the transfer of the patterns through the underlying polyimide layer using $O_2$ reactive ion etching in the same system at approximately 3 mTorr of pressure and approximately 175 watts of RF power. The sample was then coated with approximately 10 nm of gold for scanning electron microscope inspection.

Retro-Reflecting Cavities

The corners of square, rectangular, or cubical cavities can behave as retroreflectors, if they consist of three orthogonal intersecting planes.

Linear or 2D Retroreflectors

Two dimensional retroreflectors consist of two orthogonal intersecting planes (as opposed to three for a corner cube retroreflector), and they will reflect incident light directly back to the source only if the surface normal vectors of the two reflectors lie in the same plane as the vector describing the direction of the incident beam. However, the use of higher numerical aperture collection optics can ensure that all of the reflected light is collected even if the alignment is not correct. See FIGS. 13-14 for examples of linear retroreflectors. Described here is the procedure for fabricating the structures shown in FIGS. 13-14. A substrate was prepared as described in paragraph.

A stencil mask, containing pattern of rectangles and lines, was used to expose the PMMA resist using ion beam proximity lithography. The pattern was developed and transferred through the silicon dioxide and polyimide as described above.

The entire sample was coated with approximately 200 nm of gold.

Other types of retroreflectors include the “cat’s-eye” geometry and the mirror-backed lens of Axel Lundvall, Fredrik Nikolajeff, and Tomas Lindstrom “High performing micromachined retroreflector”, Optics Express, Volume 11, Issue 20, 2459-2473, October 2003.

Focusing reflectors act to bring light to a focus or near-focus at a given distance. This focus can be used to identify reflectors or groups thereof by focal length-sensitive detection, and can also enhance detectability.

Self-assembly of retroreflectors would allow powerful homogeneous assays. For example, half-retroreflectors bearing antibodies against two epitopes of anthrax toxin would be bridged together in the presence of the toxin, giving rise to highly-detectable retroreflection in a homogeneous (no-washing) assay format.

Figure 6:
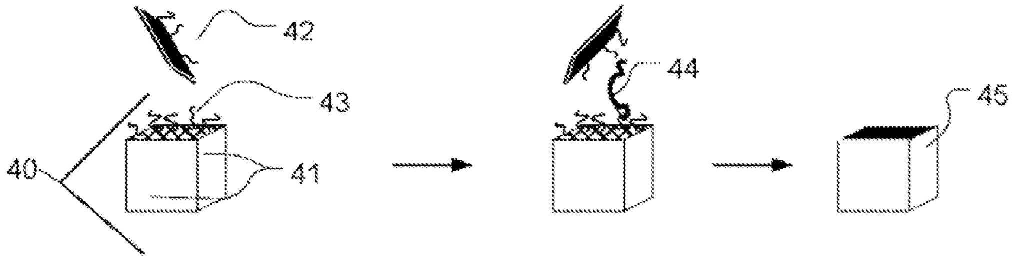
FIG. 6 depicts an embodiment for preparing another form of retroreflector cubes of this invention.

Hemisphere or cubical retroreflectors could be cut into multiple pieces, e.g., three slices of the hemispherical reflector could be stacked up in the presence of either one or two analytes (bridging at the two interfaces). Alternatively, cubical detectors could be mirrored only on two sides while the third mirror is attached only in the presence of analytes. An example of a self-assembling retroreflector is shown in FIG. 6. The fabrication sequence for these retroreflectors is identical to that shown in FIG. 2, except that the metal coats only two surfaces of the cube. A set of planar mirrors is created on a separate wafer that assembles to form the retroreflector when the target material on both surfaces is bridged by the presence of the target material. Further, only one side of the cube could be coated with the reflecting material, requiring the attachment of two planar mirrors. The planar mirror might have to be larger than a face of the cube because the mirror will not necessarily center itself. Refractive index adjustment of the solution might be helpful.

Self-Assembling Retroreflectors Using Metal Nanoparticles

Other research groups have demonstrated that the deposition of gold nanoparticles on a transparent surface will significantly increase the reflectivity of such a surface even when the particle density is very low. The reflectivity of surfaces coated with about 40 gold particles/$mm^2$ and about 4 particles/$mm^2$ and differs by about a factor of 5. This prior work, however, has not been used to produce valuable retroreflectance. (J. Reichert, A. Csaki, J. M. Kohler, and W. Fritzsche, “Chip-based optical detection of DNA hybridization by means of nanobead labeling,” *Analytical Chemistry*, vol. 72, pp. 6025-6029, 2000; A. Csáki, R. Möller, and W. Fritzsche, “Gold nanoparticles as novel label for DNA diagnostics,” *Expert Rev. Mol. Diagn, vol.* 2, 2002)

Three-Dimensional Reflectors

Three-dimensional labels can also be created that contain a reflective outer surface that reflects dark-field illumination into the detector. For example, a triangular rod shape, shown in FIG. 8, will reflect light at angle q into a detector. The shape is chosen so that, if it lies flat on the surface, annular dark-field illumination will provide an extremely bright signal to the detector even on highly reflective substrates. The probe material can be placed onto the outer surfaces of the rod and a probe site on the substrate surface will be bridged in the presence of a particular DNA/antibody/etc.

Variable Angle Detectors

The fact that retroreflectors return their reflected radiation back to its source is useful because the orientation of the reflector need not be known precisely. However, when the reflectors are placed in a known orientation on a surface, the requirement that the light be returned is no longer absolutely necessary. Instead, a reflector could be designed to return the radiation to any known location.

Variations and Extensions

These labels can be made and used in a variety of ways, many of which are summarized in Table B. In addition to assays discussed above, we anticipate their use in vibration monitoring (e.g., of machines and buildings), fluid flow monitoring, label-guided surgery (e.g., where tumor cells are labeled to be cut out—a radioisotope analog currently exists), and secure ID cards (where reflectors are used to give unique, hard-to-copy properties to an ID card). They can also be used for target tracking. The addition of a frequency selective filter (i.e., frequency selective surface) in front of the reflector would be their reflection signal frequency dependent, allowing for tracking only at pre-specified frequencies.

TABLE B

Extensions and Preferred Values of Major Parameters

| Parameter | Preferred |
|---|---|
| Material | Silicon Dioxide, with and without impurities (e.g., quartz, glass, etc.), Poly(methylmethacrylate), Polyimide, Silicon Nitride |
| Reflective layer | Gold, silver, Aluminum, Platinum, Nickel, Molybdenum, Iridium, Rhenium, interference layer, dichroic, chromium |
| Modifications of label | Polarization modulator, optical rotation element, magnetic separability, shape encoding, biocompatible surface coating, fluor, absorber, photovoltaic element, antenna, pyroelectric element, color, frequency-selective surface, interference filter, encapsulation |

TABLE B-continued

| Extensions and Preferred Values of Major Parameters | |
|---|---|
| Parameter | Preferred |
| Wavelength modulator | Fluor, molecular beacon, filter, interference filter, dichroic mirror, SPR layer, frequency selective surface, grating, code division multiple access (CDMA) |
| Reflection Angle modulator | Relative angle of cube walls, refractive index, mirror, grating |
| Shape | Cube, rhomboid, trapezoid, sphere, hemisphere, parabolic, ellipsoid, cat's eye, mirror-backed lens, skew-side cube, rectangular solid, parabolic collector, diamond cut, encoded shape, unique non-symmetric shape, assemble-able pieces, triangular rods, square rods. |
| Target Analyte | Cell surface receptor, protein, nucleic acid, mRNA, genomic DNA, PCR product, cDNA, peptide, hormone, drug, spore, virus, SSU RNAs, LSU-rRNAs, 5S rRNA, spacer region DNA from rRNA gene clusters, 5.8S rRNA, 4.5S rRNA, 10S RNA, RNAseP RNA, guide RNA, telomerase RNA, snRNAs -e.g. U1 RNA etc, scRNAs, Mitochondrial DNA, Virus DNA, virus RNA, PCR product, human DNA, human cDNA, artificial RNA, siRNA, enzyme substrate, enzyme, enzyme reaction product, Bacterium, virus, plant, animal, fungus, yeast, mold, Archae; Eukyarotes; Spores; Fish; Human; Gram-Negative bacterium, Y. pestis, HIV1, B. anthracis, Smallpox virus, Chromosomal DNA; rRNA; rDNA; cDNA; mt DNA, cpDNA, artificial RNA, plasmid DNA, oligonucleotides; PCR product; Viral RNA; Viral DNA; restriction fragment; YAC, BAC, cosmid, hormone, drug, pesticide, digoxin, insulin, HCG, atrazine, anthrax spore |
| Sample | Blood sample, air filtrate, tissue biopsy, cancer cell, surgical site, soil sample, water sample, whole organism, spore, genetically-modified reporter cells, Body Fluids (blood, urine, saliva, sputum, sperm, biopsy sample, forensic samples, tumor cell, vascular plaques, transplant tissues, skin, urine; feces); Agricultural Products (grains, seeds, plants, meat, livestock, vegetables, rumen contents, milk, etc.); soil, air particulates; PCR products; purified nucleic acids, amplified nucleic acids, natural waters, contaminated liquids; surface scrapings or swabbings; Animal RNA, cell cultures, pharmaceutical production cultures, CHO cell cultures, bacterial cultures, virus-infected cultures, microbial colonies |
| Sample preparation agent | acid, base, detergent, phenol, ethanol, isopropanol, chaotrope, enzyme, protease, nuclease, polymerase, adsorbent, ligase, primer, nucleotide, restriction endonuclease, detergent, ion exchanger, filter, ultrafilter, depth filter, multiwell filter, centrifuge tube, multiwell plate, immobilized-metal affinity adsorbent, hydroxyapatite, silica, zirconia, magnetic beads |
| Sample preparation method | Filter, Centrifuge, Extract, Adsorb, protease, nuclease, partition, wash, leach, lyse, amplify, denature/renature, electrophoresis, precipitate, germinate, Culture |
| Utility | Clinical Diagnosis; Pathogen discovery; Biodefense; Research; Adulterant Detection; Counterfeit Detection; Food Safety; Taxonomic Classification; Microbial ecology; Environmental Monitoring; Agronomy; Law Enforcement |
| Location | Well plate, filter, immunochromatographic assay, immunoassay, hybridization assay, biopsy specimen, in situ in patient, in surgical incision, surface, cell surface, thin section, self-assembled array, sea, river, lake, minefield, road, GI tract, bloodstream, airway, lung, sinus, eye, pharmaceutical, explosive, lubricant |
| Delivery | Pipette, robotic, spray, intramuscular injection, IV infusion, spray, implantation |
| Recognition element | Antibody, nucleic acid, carbohydrate, aptamer, ligand, chelators, peptide nucleic acid, locked nucleic acid, backbone-modified nucleic acid, lectin, receptor, viral protein, mixed, cDNA, metal chelate, boronate, peptide, enzyme substrate, enzyme reaction product, lipid bilayer, cell, tissue, insect, microorganism, yeast, bacterium, insect, bird, bat, trained animal, trained bird, trained insect, spore, pollen grain, biotin, metabolite analog, sugar, carbohydrate, mucin |
| Immobilization chemistry | Avidin/biotin, amine, carbodiimide, thiol, gold/thiol, metal chelate affinity, aldehyde, mixed-ligand, adsorptive, covalent |
| Size | 10 nm-3 mm |
| Number of pieces to assemble | 1-1000000 |
| Surface coating | Antibody, nucleic acids, PEG, dextran, protein, polymer, lipid, metal, glass |
| Illumination | Laser, xenon lamp, LED, arc lamp, mercury lamp, incandescent, fluorescent, scanned, time-modulated, frequency-modulated, chopped, time-gated, polarized, infrared, visible, UV, CDMA encoded, multiangle, ring |
| Detection | Eye, camera, digital camera, PMT, scanner, microscope, telescope, detector array, time-gated, chopped, frequency-modulated, wavelength-filtered, polarization-sensitive, Raman, |

TABLE B-continued

| Extensions and Preferred Values of Major Parameters | |
|---|---|
| Parameter | Preferred |
| | Surface-enhanced Raman, high numerical aperture, color-sensitive, lifetime, FRET, FRAP, intensified |
| Additions | Prodrug, drug candidate, fluor, pro-fluor, nanoparticle, molecular beacon, nanoshell, nanorod, proenzyme, quencher |

EXAMPLES

Example 1

Corner-cube retroreflectors are produced according to the procedure of FIGS. 2a-2f, using gold as the reflective metal, and recombinant immunoglobulin-binding streptococcal Protein G is coupled to the gold surfaces of the retroreflectors using NHS-PEG-thiol. Recombinant Norwalk virus surface antigens are immobilized on a membrane surface, the membrane is blocked with nonfat dry milk, and saliva samples from persons suspected of having being infected with the Norwalk virus are blended with the Protein G-decorated retroreflector cubes and dot-blotted onto the membrane. After extensive washing, retroreflectance is measured at each spot using the optical configuration of FIG. 3. Elevated retroreflectance at the spot corresponding to a given sample suggests Norwalk exposure in the patient from whom the sample originated.

Example 2

Subsequences of each of the known sequences of West Nile virus are determined, and sequences common to nearly all strains of the virus and not found in the human sequence or known SNPs are identified. Many-strain-characteristic complementary probe sequences are immobilized on a microscope slide, and hybridized with human clinical samples. Positive hybridization is detected by addition of a mixture of second DNA probes recognizing various West Nile strains, each labeled with a different shape label.

Example 3

Subsequences of each of the known sequences of Ebola virus are determined, and sequences common to nearly all strains of the virus and not found in the human sequence or known SNPs are identified. Two different many-strain-characteristic complementary probe sequences are immobilized on the two portions of a retroreflector, and added to nucleic acids isolated from a human clinical sample. The presence of Ebola virus is indicated by increase of retroreflection brightness above a predetermined threshold.

Example 4

Subsequences of each of the known sequences of Ebola virus are determined, and sequences common to nearly all strains of the virus and not found in the human sequence or known SNPs are identified. Two different many-strain-characteristic complementary probe sequences are immobilized on the two portions of a retroreflector, and added to nucleic acids isolated from a human clinical sample. The presence of Ebola virus is indicated by increase of retroreflection brightness above a predetermined threshold.

Example 5

A patient being prepared for tumor-removal surgery is infused with a retroreflector-labeled antibody specific to tumor antigens. During surgery, tissue to be removed is identified by the presence of the retroreflecting label.

Example 6

Probes to a subset of human mRNA sequences with predicted DNA probe/mRNA hybridization melting temperature in the range 63-70° C. are synthesized as DNA probes and spotted onto a microscope slide, and hybridized with mRNA isolated from human leukemia samples. Second probes labeled with a retroreflector are added and hybridized to the mRNA, and detected using an imager fitted with a semi-silvered mirror. The pattern of gene expression inferred from the hybridization results is used to choose the course of treatment of the leukemia.

Example 7

Multiwell plates in which an anchorage-dependent cell line are cultivated are robotically dosed with micromirror-labeled antibody to a cell surface EGF receptor. A drug candidate is added to each well, and the time course of the reflection pattern in each well is used to infer drug activity.

Example 8

The end of an optical fiber is coated with antibody to a toxin, and encapsulated in a membrane permeable to the toxin. The capsule also contains micromirrors decorated on their reflective faces with antibodies to another epitope of the toxin. The fiber is immersed in a flowing liquid stream, and light continuously directed down the fiber and the reflected intensity continuously monitored. Increases in brightness are interpreted as evidence of the presence of the toxin.

Example 9

A mixture of human cells is treated with two antibodies to different surface antigens. Each antibody is labeled with a skew-sided retroreflector returning light at one of two differing slight angles to the angle of incidence, not directly to the source.

The cell mixture is passed through a flow cytometer equipped for illumination at a wavelength chosen for its low propensity to damage cells, and with detectors positioned at multiple small angles to the source. The pattern of light reflected from each cell is used to classify it for sorting.

Example 10

A mixture of human cells is treated with two antibodies to different surface antigens. Each antibody is labeled with a reflector-backed-lens retroreflector returning light toward the source, but with differing focal lengths. The cell mixture is passed through a flow cytometer equipped for illumination at a wavelength chosen for its low propensity to damage cells, and with detectors positioned at multiple distances from the cell stream. The pattern of light reflected from each cell is used to classify it for sorting.

Example 11

A mixture of human cells is treated with two antibodies to different surface antigens. Each antibody is labeled with a different cubical, dye-impregnated retroreflector returning light directly to the source with an intensity dependent on wavelength.

The cell mixture is passed through a flow cytometer equipped for illumination at a wavelengths chosen for low propensity to damage cells, and with detectors positioned at very small angles to multiple sources differing in wavelength. The pattern of light reflected from each cell is used to classify it for sorting.

Example 12

A mixture of human cells is treated with two antibodies to different surface antigens. Each antibody is labeled with a different cubical, nanoshell-impregnated retroreflector returning light directly to the source with an intensity dependent on wavelength. The cell mixture is passed through a flow cytometer equipped for illumination at a wavelengths chosen for low propensity to damage cells, and with detectors positioned at very small angles to multiple sources differing in wavelength. The pattern of light reflected from each cell is used to classify it for sorting.

Example 13

A mixture of human cells is treated with two antibodies to different surface antigens. Each antibody is labeled with a different cubical, fluor-impregnated retroreflector returning light directly to the source with an intensity dependent on wavelength. The cell mixture is passed through a flow cytometer equipped for illumination at a wavelengths chosen for low propensity to damage cells, and with detectors positioned at very small angles to multiple sources differing in wavelength. The pattern of light returned from each cell is used to classify it for sorting.

Example 14

A transparent rectangular solid mirrored on two perpendicular sides is decorated with anti-toxin antibodies in a small patch near the center of a third side perpendicular to these two. A flat mirror equal in size or larger than the cube sides is also decorated with anti-toxin antibodies in a small patch near the center of its reflective surface. When an environmental sample is added to a mixture of the two reflectors, an increase in retroreflection as observed through a low-numerical aperture objective signals the presence of the toxin.

Example 15

A transparent rectangular solid mirrored on two perpendicular sides is decorated with anti-toxin antibodies in a small patch near the center of a third side perpendicular to these two. A flat mirror equal in size or larger than the cube sides is also decorated with anti-toxin antibodies in a small patch near the center of its reflective surface. When an environmental sample is added to a mixture of the two reflectors, retroreflection signals the presence of the toxin.

Example 16

Two particles, each a transparent rectangular prism, are each decorated with anti-virus antibodies in a small patch near the center of the sides which when brought together assemble the two pieces into a rectangular solid retroreflector. An environmental sample is added to a mixture of the two reflectors, and retroreflection measured from two different angles at an interval of 100 usec. An increase in retroreflection from both angles signals the presence of the virus.

Example 17

An aptamer recognizing atherosclerotic plaque is couple by amine/silane chemistry to a cat's-eye retroreflector and infused into a patient's bloodstream. Infrared illumination capable of passing through tissue with only modest attenuation is used to detect the location of vessel plaques.

Example 18

Purified human DNA is adsorbed on a surface and probed with DNA probes on five different types (focal lengths) of retroreflectors, each of which carries a mixture of four types of probes. Retroreflection is assessed as a function of focal length to identify which retroreflectors are bound. Deconvoluting the multiplexed hybridization signal allows the scoring of each of 12 different single nucleotide polymorphisms in the human DNA.

Example 19

Eight wafers are fabricated that each contain a large array (10 billion elements) of identically shaped tiles. The shape of the tiles for each wafer is unique so that the tiles from different wafers can be differentiated. The tiles on each wafer are also coated with unique probes (DNA or analog, peptide, protein, etc.) in a rapid, parallel process, so that a particular shape corresponds to a particular probe (i.e., shape encoding). Next, the tiles are released from their support wafer, disperse/suspended into solution, and are mixed with tiles from the other wafers to create a solution with eight unique probes. A small amount of this solution is then mixed with the specimen to be examined. One of the set of tiles contains a probe to which anthrax will attach. In the next step, a set of nanoparticles is exposed to the solution that will also attach to anthrax. This process is carried out in parallel for all of the other tiles probes.

Finally the sample is dried on a support substrate and loaded in to a scanning electron microscope. The images of the surface are examined by software to find all tiles that have an attached nanoparticle. A database is built that contains statistical information of the likelihood of a nanoparticle attaching to the tile containing the anthrax probe, identified by its shape. The information in this database is used to determine whether or not anthrax is present in the specimen. In addition, information about seven other materials is collected in parallel. Because of the speed of modern electronics, a very large number of shapes (10-1000) are examined every second.

Example 20

Dark field illumination. A large number (100s of millions) of triangular rods are fabricated on a wafer using micromachining technology. All rods are coated with reflective surfaces and with a probe material that attaches to anthrax DNA. When these probes come into contact with the target DNA anthrax DNA, that has been bound to a planar surface (there are numerous ways to accomplish this—see previous example for specifics), the rod attaches and is no longer free to move. Because of the shape (the rod is sufficiently long) the rod lies flat on the surface. The sample is then annularly illuminated at a specific angle relative to the surface normal that has been chosen so that light incident on the rod reflects into a detector. This will result in a very high contrast signal when a triangle is present, making the presence of anthrax easy to detect on the surface.

Example 21

Eight wafers are fabricated that each contain a large array (300 million elements) of identically shaped tiles. The shape of the tiles for each wafer is unique so that the tiles from different wafers can be differentiated. The tiles on each wafer are also coated with unique probes (DNA or analog, peptide, protein, etc.) in a rapid, parallel process, so that a particular shape corresponds to a particular probe (i.e., shape encoding). Next, the tiles are released from their support wafer, disperse/suspended into solution, and are mixed with tiles from the other wafers to create a solution with eight unique probes. A small amount of this solution is then mixed with the specimen to be examined. One of the set of tiles contains a probe to which anthrax will attach. In the next step, a set of retroreflectors is exposed to the solution that will also attach to anthrax. This process is carried out in parallel for all of the other tiles probes.

Finally the sample is dried on a support substrate and examined in an optical microscope. The images of the surface are examined by software to find all tiles that have an attached retroreflector. A database is built that contains statistical information of the likelihood of a retroreflector attaching to the tile containing the anthrax probe, identified by its shape. The information in this database is used to determine whether or not anthrax is present in the specimen. In addition, information about seven other materials is collected in parallel. Because of the speed of modern electronics, a very large number of shapes (10-1000) are examined every second.

Example 22

Eight wafers are fabricated that each contain a large array (300M elements) of identically shaped tiles. The shape of the tiles for each wafer is unique so that the tiles from different wafers can be differentiated. The tiles on each wafer are also coated with unique probes (DNA or analog, peptide, protein, etc.) in a rapid, parallel process, so that a particular shape corresponds to a particular probe (i.e., shape encoding). Next, the tiles are released from their support wafer, disperse/suspended into solution, and are mixed with tiles from the other wafers to create a solution with eight unique probes. A small amount of this solution is then mixed with the specimen to be examined. One of the set of tiles contains a probe to which anthrax will attach. In the next step, a set of triangular, reflective rods is exposed to the solution that will also attach to anthrax. This process is carried out in parallel for all of the other tiles probes.

Finally the sample is dried on a support substrate and examined in an optical microscope. The images of the surface are examined by software to find all tiles that have an attached triangular, reflective rod. A database is built that contains statistical information of the likelihood of a triangular, reflective rods attaching to the tile containing the anthrax probe, identified by its shape. The information in this database is used to determine whether or not anthrax is present in the specimen. In addition, information about seven other materials is collected in parallel. Because of the speed of modern electronics, a very large number of shapes (10-1000) are examined every second.

Example 23

An array of reflectors is created on a planar surface. Within the array, several reflectors are present whose shape is unique and will reflect incident light at a specific, pre-defined example. Hence, when the array is illuminated from a specified direction, light will reflect in predefined directions, determined by the shapes of the elements that make up the array of reflectors. One monitors the location at which the rays reflect and determines whether or not a particular pattern of reflectors is present on the surface. The intensity of each reflected beam can also be modulated by changing the pattern. This way, unique ID tags can be created that would be difficult to replicate.

Example 24

A large number of individual micro-retroreflectors is spread over a surface whose vibrational modes are to be examined. The vibration of the surface is then detected as phase changes in the returning signal. The reflective surface consists of isolated retroreflectors, which means that the surface can be monitored at various points without any coupling from the reflective material.

Example 25

Glass retroreflectors conjugated using aminosilane chemistry with anti-virus antibodies are added to a sample suspected of containing the virus, which also contains magnetic particles conjugated with antibodies to the same virus. Application of a magnetic field localizes the magnetic particles to a certain region; the presence of retroreflectance in this region is interpreted as signalling the presence of the virus in the sample.

Example 26

Glass retroreflectors conjugated using aminosilane chemistry with anti-cell surface marker antibodies are added to a sample of human blood. Cells are passed through a flow cytometer and retroreflectance from individual cells is measured along with fluorescence.

Example 27

Three-micron cubic retroreflectors composed of biodegradable poly(lactide co-glycolide) polymer and gold nanoparticles conjugated with anti-cancer cell surface marker antibodies are injected into the blood of a human cancer patient. Near-infrared optical tomography is used to identify locations at which the retroreflectors accumulate as locations of metastatic tumors.

Example 28

A human clinical tissue specimen is treated to isolate a sample enriched in mRNA, and the mRNA-enriched sample is contacted with an array of deoxyoligonucleotide probes, and then the array is contacted with retroreflectors coupled using aminosilane and avidin to biotinylated deoxyoligonucleotide probes. Retroreflectance from elements of the array is determined by in-lens CCD imaging and used to determine the levels of expression of individual genes in the cells.

Example 29

Small retroreflective particles are dusted onto honeybees which have been conditioned to seek explosive vapors, by including explosive compounds in their food. The bees are released at the boundary of a suspected minefield, and their locations observed using LIDAR. Mapping the bees' locations over a period of time indicates the locations of mines.

Example 30

Glass retroreflectors conjugated using aminosilane chemistry with anti-keratin antibodies are spread over the surface of a lake which is suspected to contain a human cadaver. One of the accumulations of retroreflectance observed by flash photography at night is the cadaver.

Example 31

Glass retroreflectors conjugated using aminosilane chemistry with anti-keratin antibodies are spread over the surface of a lake which is suspected to contain a human cadaver. One of the accumulations of retroreflectance observed by ballistic imaging at night is the cadaver.

Example 32

Antibodies to human chorionic gonadotropin are conjugated to small retroreflectors and translocated by the application of a urine sample in a lateral-flow immunochromatographic immunoassay. The appearance of a band of bright retroreflectance at the position of the capture antibody is detected using an LED and an inexpensive CCD array, and interpreted as evidence of pregnancy.

Example 33

50,000 retroreflector cube cavities that are 5 μm on a side are fabricated on a 200 mm diameter wafer glass substrate by (a) sequential coating with 5 μm thick poly(methyl methacrylate) (PMMA), 0.1 μm thick silicon dioxide ($SiO_2$), and 0.2 μm thick PMMA. The thin PMMA layer is the photoresist and is patterned using lithography. (b) After development, square openings in the resist represent the pattern of retroreflector cavities. (c) The $SiO_2$ and the underlying PMMA are then removed by reactive ion etching using $CHF_3$ and $O_2$ etch chemistries, respectively, and (d) the entire substrate is coated with a layer of gold, approximately 200 nm thick. (e) As a last step, a sputter-etch process removes the gold from the top of the PMMA and the glass while the walls remain coated. The final structure is a retroreflector that has been "disabled" because the bottom reflector has been removed. Glass is chosen as a substrate because it is transparent and it is compatible with the aminosilane chemistry that selectively bonds antivirus antibodies to the bottom of the reflector while not bonding to the gold and PMMA surfaces. An individual "chip" is $250\times1000$ $\mu m^2$ in size and contains four cube cavity sets (active assay, two active always-retroreflective) references with complete reflective coatings, and an inactive (never retroreflective, not functionalized with antibodies reference).

Each sensor chip consists of two reflective reference cubes (always remain active retroreflectors—the bottom has been coated with gold) that flank the primary signal cube and a background signal cube. The primary signal cube contains the transparent glass surface with the attached anti-virus antibodies while background cube base consists of only glass (i.e., it has not been functionalized). The spacing between these structures will be approximately 100 μm. For CCD detection schemes, the bright reference spots, with intensity 4, allow for chip alignment. Collection of the background and the primary signals, $I_B$ and $I_S$, respectively, is achieved by monitoring their locations between the two reference signals.

A water sample is mixed with gold nanorods decorated (using thiol-oligoPEG-NHS reagents) with anti-virus antibodies and applied to the reflector cube array chip.

A CCD imager is used to monitor the brightness and location of individual cube cavity retroreflectors, using a microscope that is angled relative to the surface so that specular reflections are not collected by the optics. Low numerical-aperture optics are used to minimize the collection of scattered light and to ensure that the surface remains in focus at non-normal viewing angles. Broad-beam illumination is projected along the microscope's optical axis using a 50% transparent mirror, and a CCD array, placed in the image plane of the microscope, collects the retroreflected signal that passes through the optics.

A normalized signal intensity $I_N=(I_S-I_B)/I_R$, of greater than 0.05 is interpreted as evidence of the presence of the virus in the water sample.

Example 34

A beam of light is directed towards a substrate containing a 2D retroreflector through a microscope with a numerical aperture of 0.1. The retroreflector consists of a recess with vertical walls, 50 microns wide and 500 microns long, etched into a 10 micron thick polymer coating on a silicon substrate. The entire surface is coated with a conformal metal coating that renders all surfaces highly reflective, which is decorated with anti-ricin toxin antibodies. The reflected light is collected by the lens even if the sample is misaligned by about +/−5 degrees from the nominal position. In the presence of ricin toxin, highly light-absorbing gold nanoshells decorated with anti-ricin toxin antibodies bind to the reflective surfaces, producing reduced retroreflectance which is interpreted as evidence of the presence of the toxin.

Example 35

Subsequences of each of the known sequences of Ebola virus are determined, and sequences common to nearly all strains of the virus and not found in the human sequence or known SNPs are identified. Many-strain-characteristic complementary probe sequences are immobilized on a microscope slide, and hybridized with human clinical samples. Positive hybridization is detected by addition of a second DNA probe recognizing most Ebola strains and labeled with a retroreflector for easy detection.

Example 36

Micron-sized retroreflecting corner cavities, about 5 μm on a side, are fabricated on a planar substrate. Next, one reflective surface is removed and coated with antibodies that capture the Norwalk virus. The resulting structure is a deactivated retroreflector (one reflective surface has been removed). Gold nanoparticles, 30-50 nm in size, bearing secondary detector antibodies will attach on the non-reflective surface if the Norwalk virus is present. This attachment will substantially increase the reflectivity of this surface and "re-activate" the extremely detectable retroreflection of the cavity. The incorporation of several reference cube cavities (i.e., continuously-reflective and also non-functionalized reference surfaces) on the surface, in proximity to the primary corner cube cavity, facilitate accurate quantitation.

Example 37

Variable angle detectors are fabricated on a planar substrate. One reflective surface is removed and coated with antibodies that capture the Norwalk virus. Gold nanoparticles, 30-50 nm in size, bearing secondary detector antibodies will attach on the non-reflective surface if the Norwalk virus is present. This attachment will substantially increase the reflectivity of this surface and "re-activate" the extremely detectable retroreflection of the cavity. The incorporation of several reference cube cavities (i.e., continuously-reflective and also non-functionalized reference surfaces) on the surface, in proximity to the primary corner cube cavity, facilitate accurate quantitation.

Example 38

A suspension of magnetic retroreflectors is spread over the surface of a body of water which is suspected to contain a valuable metal object that is slightly magnetized. The particles accumulate on said object, and their presence is observed by flash photography at night.

Example 39

A preparation of magnetic retroreflectors is spread over the surface of a body of water which is suspected to contain a valuable metal object that can bind to magnets. The particles accumulate on said object, and their presence is observed by ballistic imaging at night.

Example 40

A device consisting of a 200 um hollow-cube retroreflector is fabricated on a planar substrate and one reflective surface is removed (i.e., a corner-cube retroreflector with one missing mirrored surface). The missing reflective surface is coated the sugar-binding ligand (Concanavalin A or boronate). A large number (hundreds of millions) of 500 nm gold cubes are fabricated using a set of lithographic and lift-off steps and are decorated with dextran using gold/sulfur SAM chemistry. A set of filtration pores is integrated into the device to ensure that the cubes cannot leave the sample volume while still allowing liquid (but not cells or antibodies) to diffuse into the retroreflector cavity.

The device is inserted into the bloodstream and the gold cubes self-assemble onto the sugar-binding ligand when the glucose level in the bloodstream decreases. The affinity and coating density of the affinity ligand, and the density and size of the dextran, is chosen to "poise" the system at partial retroreflectance at physiological glucose levels; brightness increases as the glucose level drops. A set of permanently retroreflective corner cubes fabricated into the same substrate and embedded in a color filter will provide a wavelength-distinguishable reference signal to correct for any fluctuations in LED intensity, implant depth, etc.

Example 41

One surface of a 10×10×10 $\mu m^3$ retroreflector cavity consists of a frequency selective surface. This surface consists of an array of small circular or shaped openings in the gold reflective film, and becomes highly transmissive at a specific wavelength, determined by the design of array. For example, a 300 nm thick gold film is perforated by an array of 0.25-0.5 μm diameter openings. The pitch of the openings is chosen to be transmissive for 400 nm (wavelength) radiation and highly reflective for 700 nm (wavelength) radiation.

The openings of the frequency selective surface are coated with antibodies that capture the Norwalk virus. Gold nanoparticles, 30-50 nm in size, bearing secondary detector antibodies will attach to the openings if the Norwalk virus is present. This attachment will substantially increase the reflectivity of this surface and activate the extremely detectable retroreflection of the cavity for 400 nm (wavelength) radiation. The surface is probed with both wavelengths simultaneously, and the ratio of the two retroreflected signals (at differing wavelengths) facilitates accurate quantitation.

Example 42

Small retroreflective particles are glued onto hummingbirds which have been conditioned to seek narcotic vapors, by including narcotic-related compounds in their food. The birds are released at a border crossing at which narcotics smuggling is suspected, and their locations observed using LIDAR. Mapping the birds' locations over a period of time identifies vehicles containing smuggled narcotics Example 43

Retroreflecting cubical cavities of side length 10 um are fabricated over a 1 $cm^2$ area on a planar substrate. One reflective surface is removed and the underlying substrate is coated with a peptide which is the substrate of a protease of pharmacological interest. Gold nanoparticles, 30-50 nm in size, are prepared bearing a detector antibody which binds to the original peptide but not to the protease-modified peptide. Protease inhibitor candidates are mixed with the protease and spotted onto the surface of the chip in a regular array, with the deposition location of each candidate being recorded. After incubation at 37 C for one hour, the planar substrate is washed, then incubated with the gold nanoparticles. Locations at which retroreflectance is observed correspond to the spotting locations of active protease inhibitor drug candidates.

Example 44

A small array of reflectors is fabricated on a planar substrate, where each element reflects light at a specific angle. This is accomplished by changing the angle of one of the walls of each reflector structure lithographically. This small array is repeated to form a larger array. When the larger array is illuminated by a laser in a specific orientation, a multitude of reflected beams is formed that is determined by the shapes of the individual array elements. The reflected pattern is examined to determine the authenticity of the object to which the array has been attached.

Example 45

A set of reflector geometries is fabricated in a silicon dioxide plate. These shapes are then replicated by injection molding or step and flash imprint lithography.

Example 46

Corner-cube retroreflectors made of silica metallized with specific combinations of metals are incorporated into ammonium nitrate sold for agricultural purposes, and the metal combination associated with each batch is recorded. After an ammonium nitrate-fuel oil explosion, the retroreflectors are recovered from the scene and their metallization analyzed to identify the source of the explosive.

DETAILED DESCRIPTION OF THE DRAWINGS

Referring now to FIG. 1*a*, a corner cube retroreflector 1 consist of a transparent cube 2 that has been coated with a reflective material 3 on three mutually touching sides.

Figure 1B:
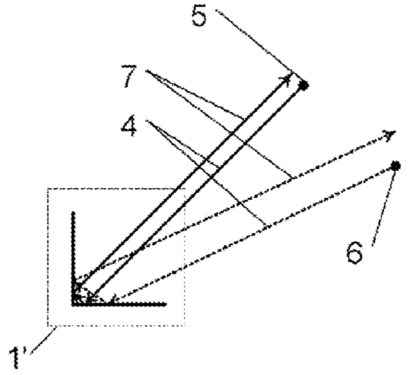
FIG. 1*b* depicts reflections from surfaces of the retroreflector of FIG. 1*a;*

Referring now to FIG. 1*b*, the retroreflector 1' is designed to ensure that incident light is always reflected back to its point of origin, within allowable acceptance angles, as is shown in this 2D schematic, where light emitted 4 from two reference points 5 and 6 reflects from the retroreflector 1' and returns to its respective emission point 7.

Figure 2A:
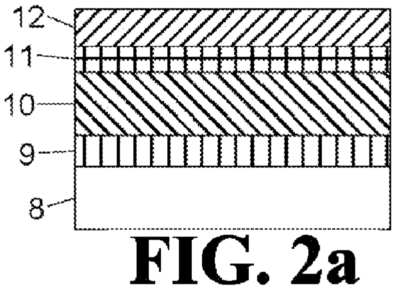
FIGS. 2*a-f* depict an embodiment of a fabrication process for making retroreflectors of this invention.
Figure 2D:
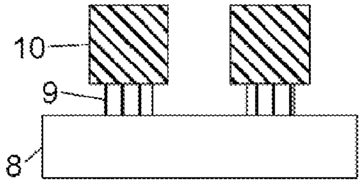
Figure 2B:
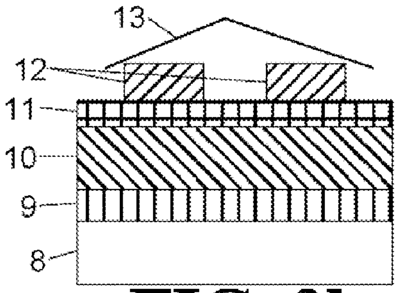
Figure 2E:
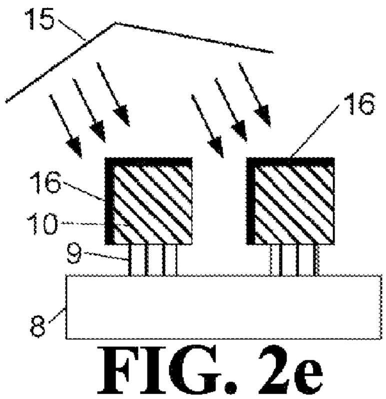
Figure 2C:
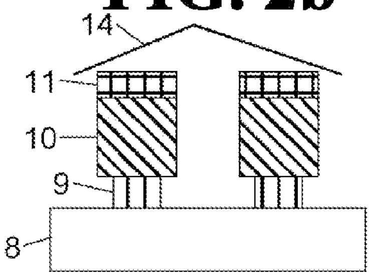
Figure 2F:
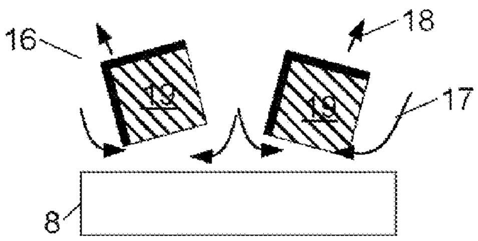

Referring now to FIGS. 2*a-f*, illustrate a similar embodiment of a process that has been used to fabricate the retroreflectors of this invention. Looking at FIG. 2*a*, an embodiment of a retroreflector of this invention is shown to include a substrate 8 that is sequentially coated with a release layer 9, a glass layer 10, a hard mask 11, and a resist 12. Looking at FIG. 2*b*, the construct of FIG. 2*a* depicts a pattern of square patches 13 is created in the resist 12 through a lithographic step. Looking at FIG. 2*c*, the resist pattern 13 is then transferred through the hard mask 11, the glass layer 10, and the release layer 9 using reactive ion etching. The etch is designed to undercut the release layer 9 while the other layers etch with almost vertical wall profiles. The resulting structures consist of an array of cubes 14. Looking at FIG. 2*d*, the hard mask material 11 is then removed. Looking at FIG. 2*e*, a collimated beam of metal atoms 15, such as one created by in-vacuum metal evaporation, coats three of the six cube faces 16 and makes them highly reflective. Looking at FIG. 2*f*, after further processing, such as changing the chemistry of the metal coated surfaces, the substrate is submerged in a liquid that dissolves 17 the release layer and frees 18 the cubes 19.

Figure 3:
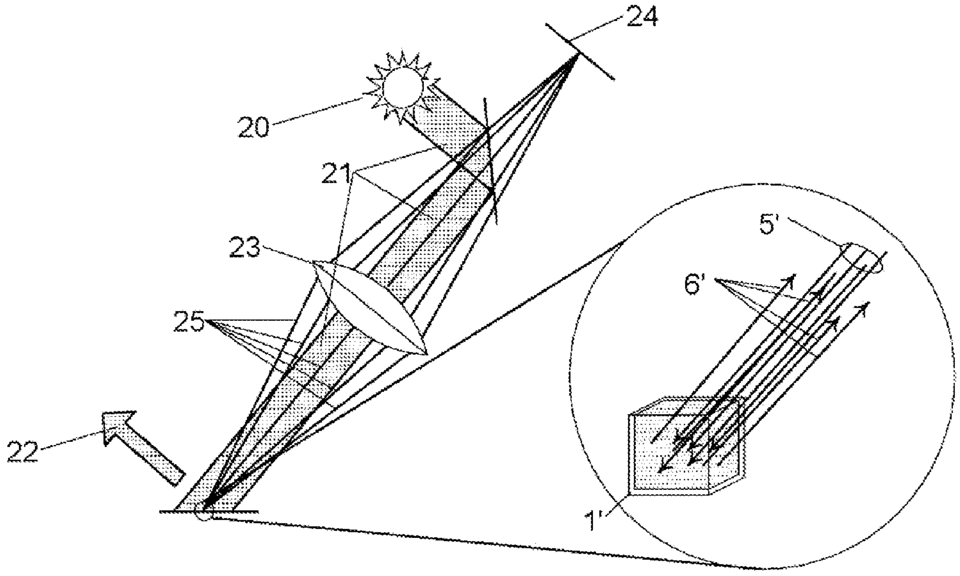
FIG. 3 depicts an embodiment of a detection configuration used to view the retroreflectors of this invention.

Referring now to FIG. 3, an embodiment of a detection configuration used to detect the retroreflectors is shown to include a microscope with an illumination source 20 that is directed along an optical axis 21, and illuminates the sample at non-normal incidence so that specular reflections 22 are not collected by the optics. Low numerical-aperture optics 23 are used to minimize the collection of scattered light and to ensure that the surface remains in focus at non-normal viewing angles. A CCD array 24, placed in the image plane of the microscope, collects the retroreflected signal 25 that is collected by the optics. Collimated incident light 5' passing through the optics from the source 20 is reflected by the microreflector 1' to produce reflected light 6', which corresponds to the retroreflected signal 25.

Figure 4A:
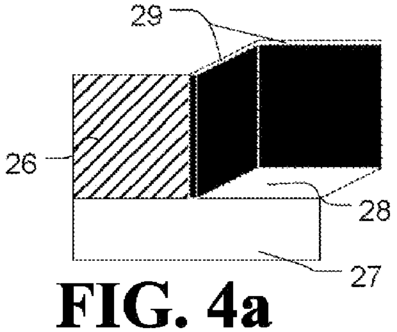
FIGS. 4*a-e* depict an embodiment of a process designed to retroreflecting corner cube cavities where one mirrored surface has been removed and post construction functionalization and detecting of captured viral particles.
Figure 4B:
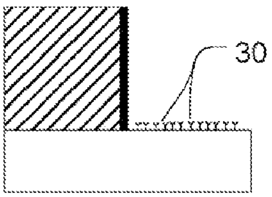
Figure 4C:
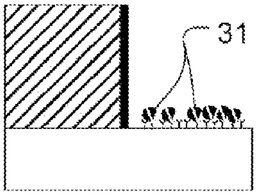
Figure 4D:
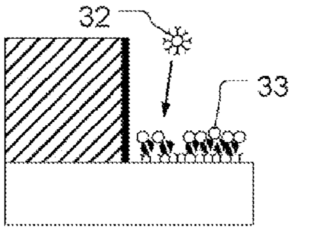
Figure 4E:
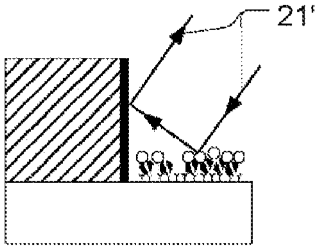

Referring now to FIGS. 4*a-e*, an embodiment of a schematic for preparing, modifying, capturing and detecting capture viruses using a retroreflector of this invention, a retroreflecting corner cube cavity where one mirrored surface has been removed, is shown and where an interior of the cavity if functionalized with antibodies designed to capture viruses. Looking at FIG. 4*a*, the cavity consists of a polymer 26 that has been selectively etched to reveal the substrate 27 and define the retroreflecting surfaces 28-29. In this design, one reflector has been removed, leaving the transparent substrate exposed 28, which effectively deactivates the device. Looking at FIG. 4*b*, non-reflective surface 28 is functionalized with antibodies 30. Looking at FIG. 4*c*, antibodies 30 can capture the virus 31 in when exposed to the sample solution. Looking at FIG. 4*d*, gold nanoparticles 32 that have also been decorated with antibodies can then be introduced, and they selectively attach to the surface where the viruses have been captured 33. Looking at FIG. 4*e* depicts the retroreflective properties are restored when the gold particles assemble, and the presence of the virus can be detected using a simple optical signal 21'.

Figure 5:
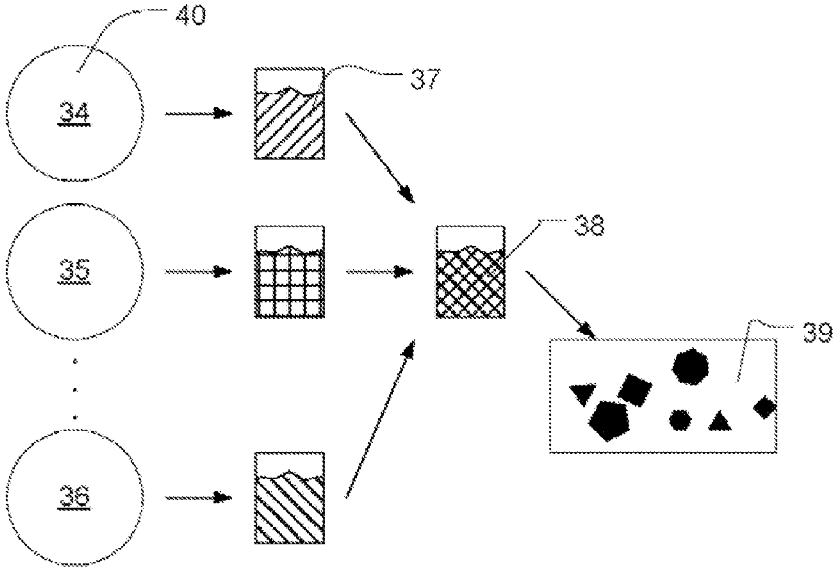
FIG. 5 depicts a process where a set of wafers are used to fabricate different shaped retroreflectors of this invention, which are then suspended in a solvent and mixed to form a collection of reflectors having different shapes.

Referring now to FIG. 5, each wafer, wafer 1-n 34-36, where n is the total number of wafers/shapes, contains a large number or unique shapes that are fabricated in parallel at very low cost. The shapes are separated from the substrate and suspended into solution 37. The shapes are mixed together and exposed to the specimen 38. The shapes are dried and inspected to determine if an attachment event occurred 39. Thus, the labels of this invention are designed to be constructed on a large scale having a variety of shapes.

Referring now to FIG. 6, retroreflector cubes 40 with only two reflecting surfaces 41 are combined in solution with a planar, reflecting probe 42. Both, the non-reflecting surfaces of the cube and the surface of the probe are functionalized with two different probes 43. In the presence of material that binds to both probe materials 44, the cube assembles with the planar mirror to form a retroreflector 45.

Referring now to FIG. 7, a substrate 46) is sequentially coated with a release layer 47 and resist 48. The resist is exposed and developed, leaving behind a silica island 49. Probes 50 are attached to island structure. The wafer is submerged in a liquid that dissolves 51 the release layer and releases the island structures from substrate 52.

Figure 8:
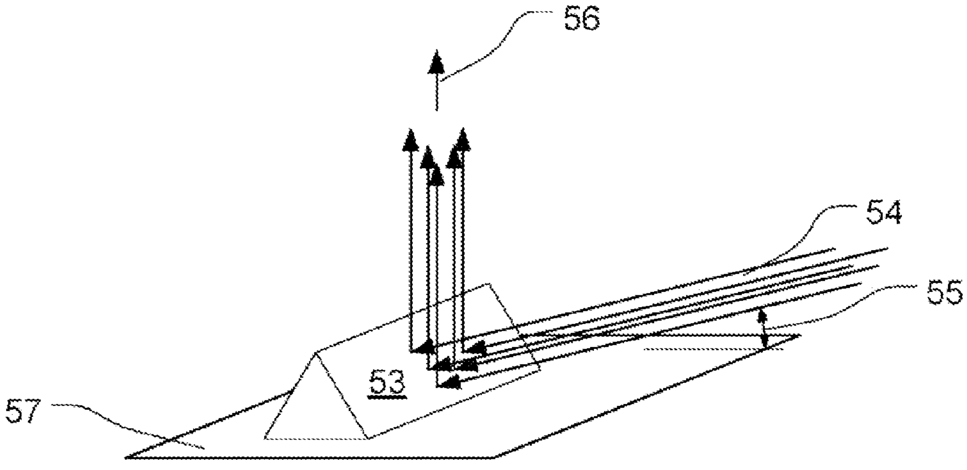
FIG. 8 depicts a 3D triangular rod reflector of this invention.

Referring now to FIG. 8, a 3D triangular rod 53 reflects dark-field illumination 54 at a specific angle 55 directly towards a detector 56 when captured on a substrate 57.

Figure 9:
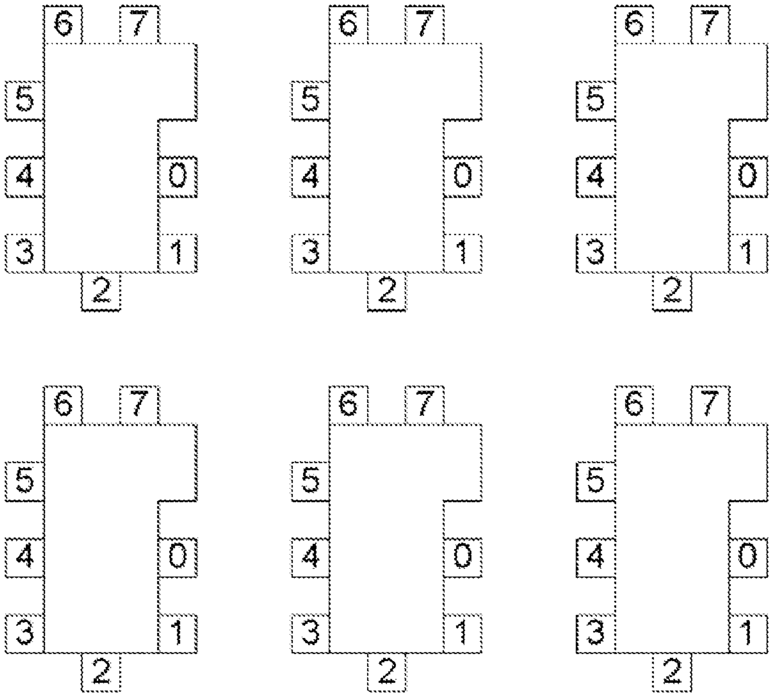
FIG. 9 depicts an example shape with eight bit encoding (0-7)

Referring now to FIG. 9, an example of a shape having eight bit encoding (0-7).

Referring now to FIG. 10, a scanning electron micrograph shows the surface, viewed along the direction of the surface normal, of an array of micro-fabricated polyimide cube structures where some of the cubes have been mechanically removed from the surface for the purpose of viewing.

Figure 11:
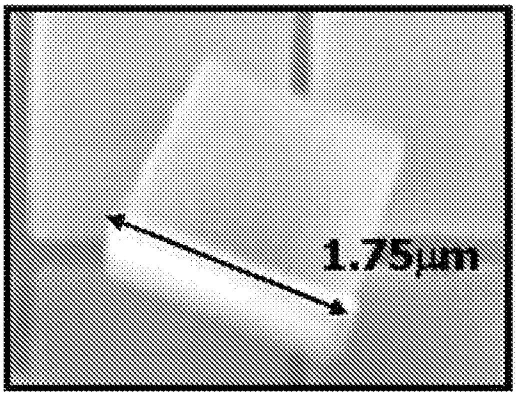
FIG. 11 shows a close-up of the region designated by the rectangular box in FIG. 10.

Referring now to FIG. 11, a scanning electron micrograph shows a close-up of the region designated by the rectangular box in FIG. 10. The image contains a single cube structure that is approximately $1.75 \times 1.75 \times 1.5\ \mu m^3$ in size.

Figure 12:
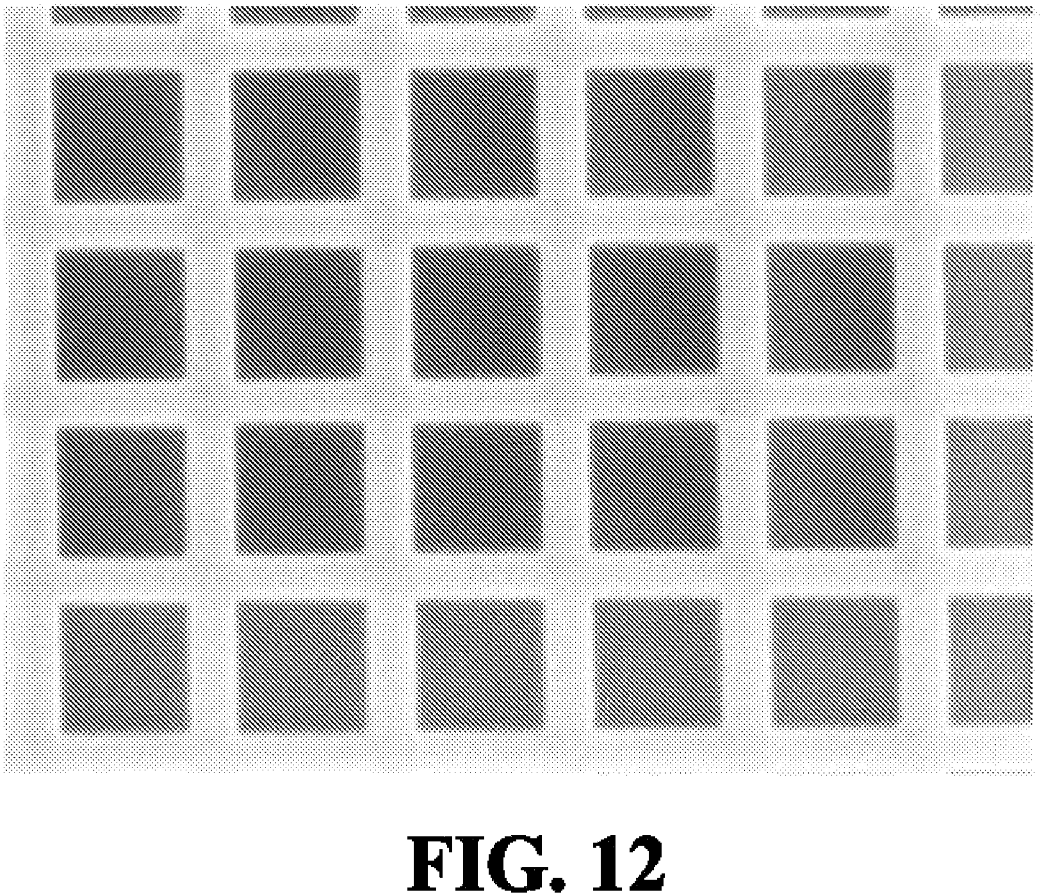
FIG. 12 shows an array of square patches in poly(methyl methacrylate) (PMMA) PMMA resist defined by ion beam aperture array lithography.

Referring now to FIG. 12, a scanning electron micrograph shows the surface, viewed along the direction of the surface normal, of an array of square patches in PMMA resist defined by ion beam aperture array lithography. This pattern serves as the basis for fabricated corner cube structures similar to those seen in FIG. 10.

Figure 13:
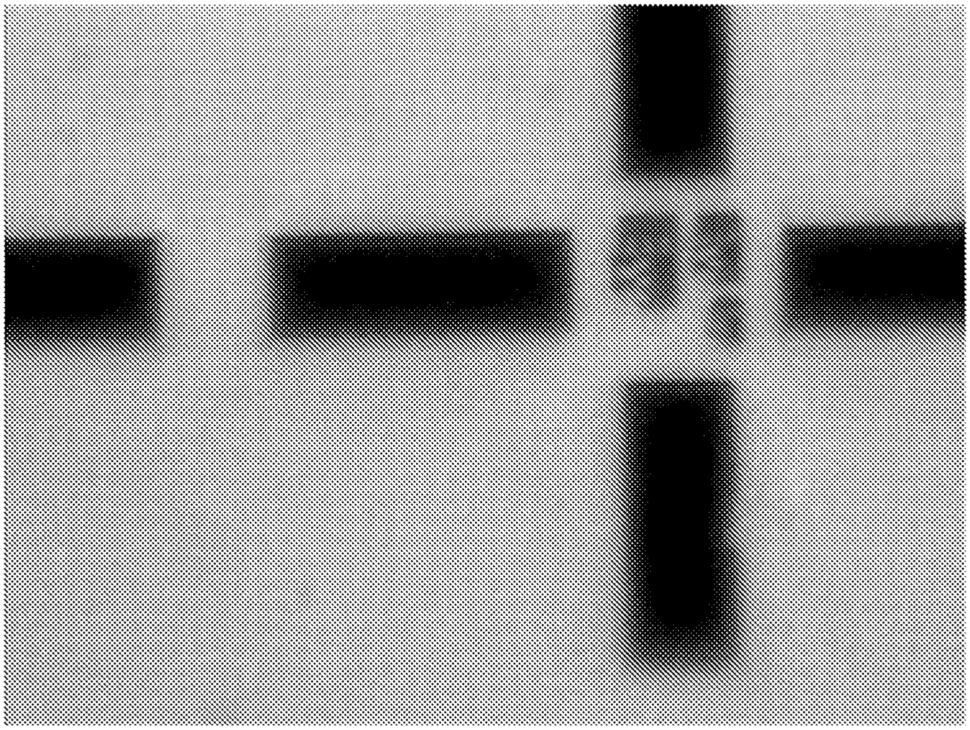

Referring now to FIG. 13, an optical microscope image shows a linear retroreflector, where the dark regions in the image are structures that were etched into a 5 micron thick layer of polyimide. The entire surface was then coated with gold. The large, rectangular regions are roughly 60×20 microns in size. The image is illuminated using a broad source so that light is reflected from the surface and is directed along the optical axis of the imaging optics.

Figure 14:
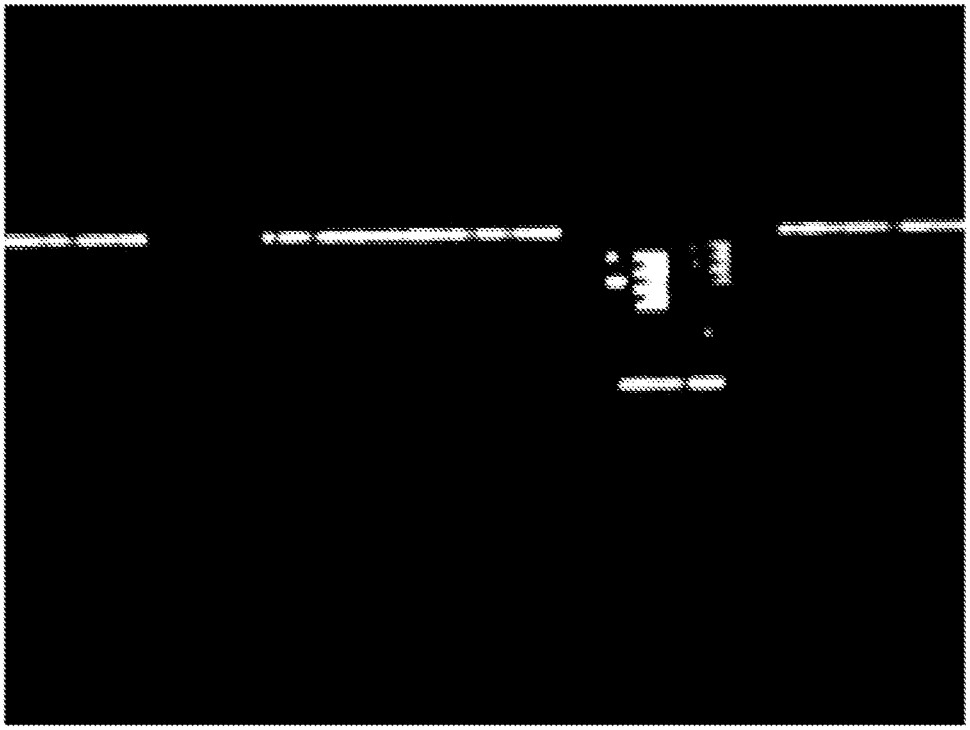
FIG. 14 shows the same linear retroreflector in FIG. 12, except that the image is illuminated along the optical axis of the imaging optics so that only the portions of the sample that retroreflect appear bright.

Referring now to FIG. 14, an optical microscope image of the linear retroreflector shown in FIG. 12, where the image is illuminated along the optical axis, as shown in FIG. 3, of the imaging optics so that only the portions of the sample that retroreflect appear bright.

Modifications of the Invention

A composition comprising a shape-encoded label smaller than 300 um in largest dimension, and further comprising a biological recognition moiety.

A composition comprising a chiral shape-encoded label, and further comprising a biological recognition moiety.

A process of performing a biological assay, comprising using a chiral shape-encoded label, and further comprising using a biological recognition moiety.

A retroreflecting element comprising three orthogonal surfaces, and further comprising a biological recognition element.

A retroreflecting element comprising two orthogonal surfaces, longer in the direction parallel to both of the two surfaces than in the direction parallel to either surface, and associated with a biological recognition element.

A retroreflecting element comprising a spherical portion, and associated with a biological recognition element.

A retroreflecting element associated with a biological recognition element which associates with a particle or surface in the presence of a target analyte.

A reflecting element associated with a biological recognition element, and a second reflecting component, where assembly of the first element and the second element in the presence of a target analyte produces retroreflectance.

An array of at least three reflecting elements associated with biological recognition elements, and a plurality of second reflecting components, where assembly of an element of the array and the one of the second reflecting elements in the presence of a target analyte produces retroreflectance.

A method of monitoring the concentration of a target analyte in a gas or fluid, comprising: (a) exposing to the gas or fluid a first element of a retroreflector, associated with a recognition agent capable of interacting with the analyte, and a second element of a retroreflector, also associated with a recognition element capable of associating with the target analyte; and (b) detecting retroreflectance from the retroreflector assembled from the first and second elements.

A method of monitoring the concentration of an analyte in a gas or fluid, comprising: (a) exposing to the gas or fluid a first element of a retroreflector, associated with a recognition agent capable of interacting with the analyte and also capable of interacting with an analyte analog, and a second element of a retroreflector, associated with a target analyte analog capable of associating with the recognition agent associated with the first element; and (b) detecting retroreflectance from the retroreflector assembled from the first and second elements.

A method of monitoring the concentration of an analyte in a gas or fluid, comprising: (a) exposing to the gas or fluid a retroreflector, associated with a recognition agent capable of interacting with the analyte, and a reflection-intensity-reducing element, also associated with a recognition element capable of associating with the analyte; and (b) detecting the reduction in retroreflectance resulting from the presence of the analyte.

A method of monitoring the concentration of an analyte in a gas or fluid, comprising: (a) exposing to the gas or fluid a retroreflector, associated with a recognition agent capable of interacting with the analyte and also capable of interacting with an analyte analog, and a reflection-intensity-reducing element, associated with an analyte analog capable of associating with the recognition agent associated with the first element; and (b) detecting increased retroreflectance from the retroreflector in the presence of the analyte.

The use of a retroreflector of retroreflectance intensity responsive to analyte concentration, additionally comprising the exposing to the fluid or gas a reflective element whose signal intensity is not responsive to the analyte.

A method of monitoring the concentration of a sugar in fluid, comprising: (a) exposing to the gas or fluid a first element of a retroreflector, associated with a recognition agent such as a lectin, antibody or boronate capable of interacting with the sugar and also capable of interacting with an analyte analog such as dextran or another polysaccharide, and a second element of a retroreflector, associated with a target analyte analog such as dextran or another polysaccharide capable of associating with the recognition agent associated with the first element; and (b) detecting retroreflectance from the retroreflector assembled from the first and second elements.

A method of locating an object, by introducing a retroreflector associated with a biological recognition element into the area where the object may be located, and observing the location of the retroreflector.

A method of detecting binding of analytes to elements of an array of biological recognition elements, comprising contacting retroreflective elements associated with biological recognition element with the array, and then detecting retroreflectance associated with elements of the array.

A method of locating an object, by introducing a retroreflector associated with a trained animal, insect or bird into the area where the object may be located, and observing the location of the retroreflector.

A method of controlling access to a machine or area, based upon requiring the presentation of an object bearing a number of micron-scale reflectors in a predetermined pattern.

A composition comprising a shape-encoded label smaller than 300 um in largest dimension, and further comprising an explosive or explosive ingredient.

A composition comprising a shape-encoded label smaller than 300 um in largest dimension, and further comprising a lubricant A composition comprising a retroreflector smaller than 300 um in largest dimension, and further comprising an explosive or explosive ingredient.

A composition comprising a retroreflector smaller than 300 um in largest dimension, and further comprising a pharmaceutical.

REFERENCES

The following documents are incorporated by reference into this application:

1. Laser Focus World; October 94, Vol. 30 Issue 10, p 129.
2. Laser Focus World Vol 30, 129-32, 1994
3. Applied Optics Vol 5, 1191-1197, 1966
4. Applied Optics Vol 14, 1825-1828, 1975
5. Applied Optics Vol 15 445-452, 1976
6. Applied Optics Vol 38 4137-4144, 1999
7. Optical engineering 38, 164-69, 1999
8. International patent WO 95/34006
9. Optics Express, Volume 11, Issue 20, 2459-2473 October 2003
10. *Analytical Chemistry*, vol. 72, pp. 6025-6029, 2000
11. *Expert Rev. Mol. Diagn*, vol. 2, 2002

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

We claim:

1. A composition comprising a unique, non-random pattern of reflectors, manufactured by a deterministic process, where a largest dimension of the reflector is below about 100 μm, and where the reflectors comprise a substrate, a top layer disposed on a top surface of the substrate and recessed regions having at least three mutually-perpendicular, adjacent faces, where at least two faces of each of the regions comprise a portion of the top layer and one face comprises a portion of the substrate, where at least two faces are coated with a reflective material so that they comprise mirrored surfaces.

2. The composition of claim 1, wherein the reflectors include metallic surfaces.

3. The composition of claim 1, wherein the pattern includes at least 20 reflectors.

4. The composition of claim 1, further comprising a biological recognition moiety.

5. The composition of claim 1, wherein a largest dimension of the reflector is below 30 μm.

* * * * *